United States Patent [19]

Novák et al.

[11] 4,344,959
[45] Aug. 17, 1982

[54] TERPENE DERIVATIVES AND INSECTICIDAL COMPOSITIONS CONTAINING TERPENES

[75] Inventors: Lajos Novák; Csaba Szántay; János Rohály; Attila Kis-Tamás; László Varjas, all of Budapest; János Csuták, Kazincbarcika, all of Hungary

[73] Assignee: Egyt Gyogyszervegyeszeti Gyar, Budapest, Hungary

[21] Appl. No.: 251,043

[22] Filed: Apr. 6, 1981

[30] Foreign Application Priority Data

Apr. 11, 1980 [HU] Hungary ..................................... 877

[51] Int. Cl.³ .................. A61K 31/365; A61K 31/23; C07D 307/20
[52] U.S. Cl. ..................................... 424/279; 424/305; 424/312; 260/410.9 R; 549/322
[58] Field of Search ..................... 424/279, 305, 312; 260/410.9 R, 343.6, 410.9 M, 410.9 Q

[56] References Cited

U.S. PATENT DOCUMENTS 3,700,694 10/1972 Siddall ............................. 260/343.6
3,736,319 5/1973 Martel et al. ...................... 560/122
4,010,170 3/1977 Larock ............................. 260/343.6

*Primary Examiner*—Jane T. Fan
*Attorney, Agent, or Firm*—Keil & Witherspoon

[57] ABSTRACT

The invention relates to new compounds of the general formula (I),

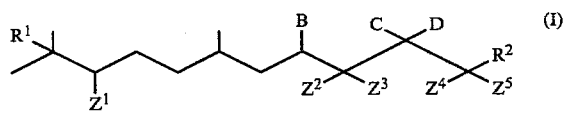

wherein    #
$R^1$ is hydrogen or a lower alkoxy group and
$Z^1$ is hydrogen, or
$R^1$ and $Z^1$ form together a double bond,
$Z^2$ is hydrogen and
B is hydroxy, or
$Z^2$ and B form together a double bond,
$Z^3$ and $Z^4$ each stand for hydrogen or they form together an ethylene group, or
$Z^4$ and D form together a double bond,
C is oxygen atom or a lower alkoxy group,
D is a valence bond if C stands for oxygen, or otherwise D forms a double bond together with $Z^4$ or $Z^5$,
$Z^5$ forms a double bond together with D or represents hydrogen, and
$R^2$ is a group of the general formula —$COOR^3$, wherein $R^3$ is lower alkyl, or
$Z^5$ and $R^2$ form together a 1-oxo-2-oxa-tetramethylene group, with the proviso that if $Z^3$ and $Z^4$ form together an ethylene group, $R^2$ may stand only for a —$COOR^3$ group, insecticidal compositions containing them, as well as to a process for their preparation.

11 Claims, No Drawings

TERPENE DERIVATIVES AND INSECTICIDAL COMPOSITIONS CONTAINING TERPENES

The invention relates to new terpene derivatives, to a process for the preparation thereof, furthermore to insecticidal compositions which contain said new terpene derivatives.

The new compounds according to the invention correspond to the general formula (I),

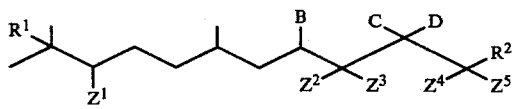

wherein
$R^1$ is hydrogen or a lower alkoxy group and
$Z^1$ is hydrogen, or
$R^1$ and $Z^1$ form together a double bond,
$Z^2$ is hydrogen and
B is hydroxy, or
$Z^2$ and B form together a double bond,
$Z^3$ and $Z^4$ each stand for hydrogen or they form together an ethylene group, or
$Z^4$ and D form together a double bond,
C is oxygen atom or a lower alkoxy group,
D is a valence bond if C stands for oxygen, or otherwise D forms a double bond together with $Z^4$ or $Z^5$,
$Z^5$ forms a double bond together with D or represents hydrogen, and
$R^2$ is a group of the general formula $-COOR^3$, wherein $R^3$ is lower alkyl, or
$Z^5$ and $R^2$ form together a 1-oxo-2-oxa-tetramethylene group, with the proviso that if $Z^3$ and $Z^4$ form together an ethylene group, $R^2$ may stand only for a $-COOR^3$ group.

The term "lower alkoxy" refers to straight-chained or branched alkoxy groups with 1 to 4 carbon atoms, such as methoxy, ethoxy, propoxy, isopropoxy, n-butoxy etc., particularly methoxy group. The term "lower alkyl" refers to straight-chained or branched alkyl groups with 1 to 4 carbon atoms, such as methyl, ethyl, n-propyl, isopropyl, n-butyl, tert.-butyl etc. groups.

Furthermore, the invention relates to insecticidal compositions which contain as active agent 0.01 to 96% by weight of one or more compound(s) of the general formula (I), wherein $R^1$, $Z^1$, B, C, D, $Z^2$, $Z^3$, $Z^4$, $Z^5$ and $R^2$ are as defined above, together with one or more appropriate inert carrier(s) or diluent(s). The insecticidal compositions may also contain other additives, such as auxiliary agents and/or other known juvenoids or insect growth regulating substances.

The insecticidal compositions according to the invention may contain as active agent preferably a compound of the general formula (Ia),

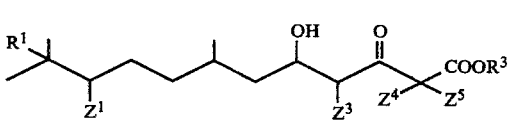

wherein $R^1$, $Z^1$, $Z^3$, $Z^4$, $Z^5$ and $R^3$ are as defined above. Particularly preferred representatives of the compounds having the general formula (Ia) are the following derivatives: ethyl-(5-hydroxy-7,11-dimethyl-11-methoxy-3-oxo-dodecanoate), isopropyl-(5-hydroxy-7,11-dimethyl-11-methoxy-3-oxo-dodecanoate), and tert.-butyl-(5-hydroxy-7,11-dimethyl-11-methoxy-3-oxo-dodecanoate).

The insecticidal compositions according to the invention may also contain as active agent preferably a compound of the general formula (Ic),

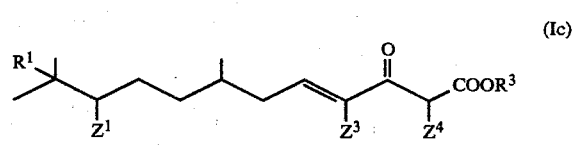

wherein $R^1$, $Z^1$, $Z^3$, $Z^4$ and $R^3$ are as defined above.
Ethyl-[11-methoxy-3-oxo-7,11-dimethyl-4(E)-dodecenoate] is a particularly preferred representative of the compounds having the general formula (Ic).

With regard to their specific biological effects, the compounds of the general formula (I) can be regarded in broader sense as insect growth regulating substances, and in narrower sense as bioanalogues of juvenile hormones (juvenoids). Disregarding their eventual direct toxicity exerted in higher doses, the compounds kill the insects indirectly by causing irreversible disturbances in the embryonal or postembryonal development, in certain reproduction processes or in the cyclic rhythm, which have direct lethal consequences or substantially reduce the population number of the next generation. The compositions according to the invention which contain one or more compound(s) of the general formula (I) as active agents, can be utilized as inhibitors of insect metamorphosis, ovicidal agents, chemical sterilizing agents or anti-diapausal agents. The compositions exert their effects on the insects upon contact or oral intake, sometimes also as fumigants.

The compounds of the general formula (I) can be converted into insecticidal compositions, such as emulsifiable concentrates (EC), granulates (preferably microgranulates), etc. These compositions contain the active agent(s) in combination with solid or liquid inert carriers or diluents, solvents and other auxiliary agents.

Of the auxiliary agents e.g. surfactants (such as wetting, emulsifying and dispersing agents), anticaking agents, lubricants, adhesives, sticking aids, dyestuffs, corrosion inhibitors, suspending agents, substances increasing the resistance against rain, penetration aids, etc. are to be mentioned.

As solid carriers or diluents e.g. inert mineral substances, such as aluminium silicate, talc, ignited magnesia, silica, tricalcium phosphate, cork meal, coke powder, clays, kaoline, pearlite, pyrophillite, dolomite, gypsum, calcium phosphate, calcium carbonate, mica, colloidal silicon dioxide, Fuller's earth, Hewitt's earth, china clay, etc. can be applied.

As liquid carriers or diluents e.g. aqueous, organic and/or aqueous-organic solvents, such as water, ketones (e.g. acetophenone, cyclohexanone, isophoron, etc.), aromatic hydrocarbons (e.g. benzene, toluene, xylene, etc.), alkylnaphthalenes, tetrahydronaphthalene, chlorinated hydrocarbons (e.g. chlorobenzenes, dichloroethylene, trichloroethylene, tetrachloroethane, etc.), alcohols (e.g. methanol, ethanol, isopropanol, butanol, propylene glycol, diacetone alcohol, etc.), kerosene, mineral, animal and vegetable oils, aliphatic mineral oil fractions, petrol distillates with high aromatic contents (e.g. naphtha and distilled tar oil), polar organic solvents (e.g. dimethyl sulfoxide and dimethyl formamide), and mixtures thereof can be applied.

Besides the solid and liquid carriers mentioned above inert gaseous carriers can be applied as well. Of the gaseous carriers the Freon-type gases, such as various chlorinated or fluorinated methane and ethane derivatives (e.g. fluorodichloromethane, difluorodichloromethane, etc.) are to be mentioned.

The wetting, dispersing and emulsifying surfactants can be ionic or non-ionic in type.

As non-ionic surfactants e.g. condensates of ethylene oxide with $C_{10-20}$ fatty alcohols (such as oleyl alcohol, cetyl alcohol, octadecyl alcohol, etc.), alkylphenols (such as octylphenol, nonylphenol, octylcresol, etc.), amines (such as oleylamine), mercaptans (such as dodecylmercaptan) or carboxylic acids, partial esters of higher fatty acids and hexitol anhydrides, condensation products of these partial esters and ethylene oxide, lecithins, fatty acid esters of polyalcohols, etc. can be applied.

The ionic surfactants can be cationic or anionic compounds.

Of the cationic surfactants e.g. the quaternary ammonium compounds (such as cetyl-trimethyl-ammonium bromide, cetylpyridinium bromide, etc.) are to be mentioned.

Examples of the anionic surfactants are soaps, salts of aliphatic monoesters of sulfuric acid (such as sodium laurylsulfate, sodium salt of dodecanol monosulfate), salts of sulfonated aromatic compounds (such as sodium dodecyl benzenesulfonate, sodium, calcium or ammonium ligninsulfonate), butylnaphthalenesulfonate, mixtures of the sodium salts of di- and triisopropyl-naphthalenesulfonic acid, sodium salts of petroleumsulfonic acids, potassium or triethanolamine salts of oleic acid or abietic acid, etc.

As suspending agents e.g. hydrophilic colloids (such as polyvinyl pyrrolidone, sodium carboxymethyl cellulose, etc.), furthermore gums of vegetable origin (such as tragacanth gum, etc.) can be applied.

Examples of sticking aids are lubricants (such as calcium or magnesium stearate), adhesives (such as polyvinyl alcohol), cellulose derivatives and other colloidal substances (such as caseine), mineral oils, etc.

Of the dispersing agents e.g. methyl cellulose, ligninsulfonates, alkylnaphthalenesulfonates, etc. are to be mentioned.

As distribution aids, sticking agents, agents for increasing rain resistance or penetration aids e.g. fatty acids, resins, glue, caseine and alginates can be applied.

Utilizing the carriers, diluents and auxiliary agents mentioned above, the active agents according to the invention can be converted into various solid, liquid or gaseous agricultural or horticultural compositions.

Examples of the solid compositions are grains and granulates (preferably microgranulates), pastes, etc.

Of the liquid compositions the following are to be mentioned: solutions, such as directly sprayable solutions (e.g. aqueous solutions, solutions formed with organic solvents or oils, miscible oils, etc.), dispersions, suspensions (primarily aqueous suspensions), aqueous or oily emulsions, invert emulsions, etc.

As gaseous compositions e.g. aerosol preparations can be applied.

The granular compositions can be prepared e.g. by dissolving the active agent(s) of the invention in a solvent, and applying the solution onto a granular carrier (e.g. a porous granular substance, such as pumice stone or attaclay, a non-porous mineral granulate, such as sand or loam, or a granular organic substance, such as black soil or cut tobacco stalk) in the presence of a binding agent, and, if desired, drying the resulting granular substance. According to another method, granular compositions are prepared by admixing the active agent(s) with a powdered mineral substance, a lubricant and a binding agent, compressing the mixture, crushing the compressed substance, and separating the fraction with the required grain size by sieving. A preferred method of preparing granular compositions is dry or wet granulation, the latter being performed either by wet compression or by buildup technique.

Dispersions, suspensions or emulsions can be prepared by dissolving or suspending the active agent(s) according to the invention in a solvent which contains optionally one or more wetting, dispersing, suspending and/or emulsifying agent(s), and admixing the resulting mixture with water, also containing optionally one or more wetting, dispersing, suspending and/or emulsifying agent(s). Of course, either the solvent or the water applied must contain at least one wetting, dispersing, suspending and/or emulsifying agent. These compositions preferably also contain an antioxidant, such as butyl-hydroxy-anisol, or a light stabilizer, such as Uvinul$^R$539.

Miscible oils can be prepared by dissolving or finely dispersing the active agent(s) according to the invention in an appropriate solvent, preferably in a solvent sparingly miscible with water, in the presence of an emulsifying agent.

Solutions for direct spraying are prepared by dissolving the active agent(s) according to the invention in a solvent with medium to high boiling point. It is preferred to apply a solvent boiling above 100° C.

Aerosols can be prepared e.g. by admixing the active agent(s) according to the invention, or—if necessary—a solution thereof, with a volatile liquid applied as propellant, e.g. with a Freon-type compound.

Invert emulsions can be prepared by emulsifying an emulsion of the active agent(s) according to the invention in water directly in the spraying apparatus either before or during spraying.

Emulsifyable concentrates, pastes or wettable spray powders can be applied particularly preferably to prepare aqueous formulations ready for use. These concentrates are diluted prior to use with water to the required concentration. The concentrates should be stable for a prolonged period of storage, and, after dilution with water, they should form aqueous compositions which remain homogeneous for a time sufficient to apply them with a conventional spraying apparatus. The concentrates generally contain 10 to 85% by weight, preferably 25 to 60% by weight, of active agent. The dilute aqueous compositions (spray liquids) ready for use contain preferably 0.01 to 3.00% by weight of active agent, however, for specific applications, compositions with higher or lower active agent content can also be prepared.

Depending on the method of preparation and application, the active agent contents of the compositions required to have the desired effect may vary over a broad range. The compositions contain generally 0.01 to 96% by weight of active agent. When the composition is to be applied according to the "ultra-low volume" (ULV) technique, the active agent according to the invention can be admixed with extremely small amounts of additives to form compositions containing preferably 90 to 98% by weight of active agent. These compositions are applied to the desired places with an apparatus producing extremely fine sprays, preferably from an aeroplane. Diluted compositions contain generally 0.01 to 20% by weight of active agent, whereas the active agent content of the concentrates may vary generally between 20 and 98% by weight.

The emulsifyable concentrates contain generally 5 to 70% by weight, preferably 10 to 50% by weight, of active agent. The active agent content of the powdery compositions may be generally 0.5 to 10% by weight, preferably 1 to 5% by weight.

The compositions according to the invention can be applied as sprays, powder sprays, etc. The type of composition to be applied depends on the requirements of the field of application.

The invention relates further to an agricultural process, in which the plants and/or the soil is(are) treated either directly or indirectly with a composition containing a compound of the general formula (I).

In this agricultural process the compositions according to the invention are applied onto or into the soil, onto the plants, or onto a pre-selected part of the plants.

The agricultural treatment method of the invention can be performed by applying the composition containing the active agent directly to the plant, to certain parts (e.g. the leaves) of the plants, or to the environment of the plants. The compositions can be applied to the desired place e.g. by spraying, dusting, etc.

The invention relates further to a process for the preparation of compounds having the general formula (I). According to the invention one proceeds as follows:

(a) to prepare a subgroup of the compounds having the general formula (I), i.e. compounds of the general formula (Ia), wherein $R^1$, $Z^1$, $Z^3$, $Z^4$, $Z^5$ and $R^3$ are as defined above, a dianion formed from a compound of the general formula (II), $$Z-COOR \quad (II)$$

wherein Z is an acetonyl or cyclopentanon-1-yl group and R is a lower alkyl group, preferably by treating it with an alkali metal hydride or a $C_{1-4}$ alkyl lithium, is reacted with a citronellal derivative of the general formula (III),

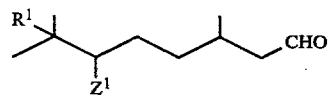

wherein $R^1$ and $Z^1$ are as defined above, or (b) to prepare a subgroup of the compounds having the general formula (I), i.e. compounds of the general formula (Ib),

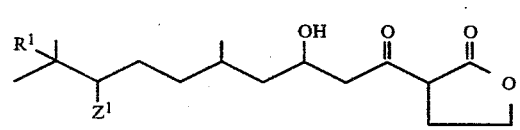

wherein $R^1$ and $Z^1$ are as defined above, a citronellal derivative of the general formula (III), wherein $R^1$ and $Z^1$ are as defined above, is reacted with a dianion formed from 2-acetyl-butyrolactone preferably by treating it with a $C_{1-4}$ alkyl lithium or an alkali metal hydride, or (c) to prepare a subgroup of the compounds having the general formula (I), i.e. compounds of the general formula (Ic), wherein $R^1$, $Z^1$, $Z^3$, $Z^4$ and $R^3$ are as defined above, a compound of the general formula (Ia), wherein $R^1$, $Z^1$, $Z^3$, $Z^4$, $Z^5$ and $R^3$ are as defined above, is subjected to an elimination reaction preferably in the presence of an acid, or (d) to prepare a subgroup of the compounds having the general formula (I), i.e. compounds of the general formula (Id),

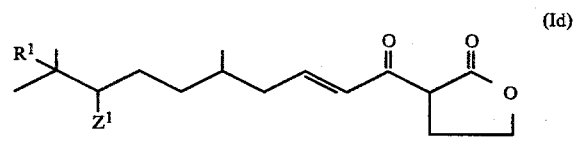

wherein $R^1$ and $Z^1$ are as defined above, a compound of the general formula (Ib), wherein $R^1$ and $Z^1$ are as defined above, is subjected to an elimination reaction preferably in the presence of an acid, or (e) to prepare a subgroup of the compounds having the general formula (I), i.e. compounds of the general formula (Ie),

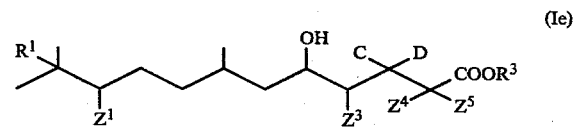

wherein $R^1$, $Z^1$, $Z^3$, $Z^4$, $Z^5$ and $R^3$ are as defined above and C is a lower alkoxy group, a compound of the general formula (Ia), wherein $R^1$, $Z^1$, $Z^3$, $Z^4$, $Z^5$ and $R^3$ are as defined above, is reacted with a $C_{1-4}$ diazoalkane, or (f) to prepare a subgroup of the compounds having the general formula (I), i.e. compounds of the general formula (If),

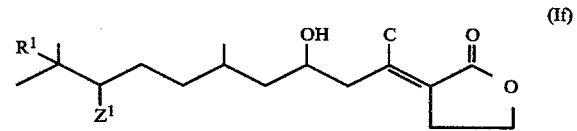

wherein $R^1$ and $Z^1$ are as defined above and C is a lower alkoxy group, a compound of the general formula (Ib), wherein $R^1$ and $Z^1$ are as defined above, is reacted with a $C_{1-4}$ diazoalkane, or (g) to prepare a subgroup of the compounds having the general formula (I), i.e. compounds of the general formula (Ig),

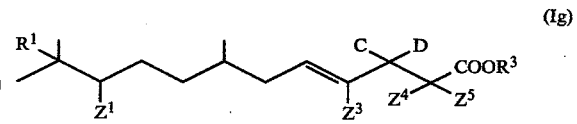

wherein $R^1$, $Z^1$, $Z^3$, $Z^4$, $Z^5$, D and $R^3$ are as defined above and C is a lower alkoxy group, a compound of the general formula (Ic), wherein $R^1$, $Z^1$, $Z^3$, $Z^4$ and $R^3$ are as defined above, is reacted with a $C_{1-4}$ diazoalkane or is treated with an alkanol in the presence of a catalytic amount of an acid, or (h) to prepare a subgroup of the compounds having the general formula (I), i.e. compounds of the general formula (Ih),

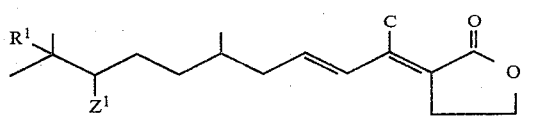

wherein $R^1$ and $Z^1$ are as defined above and C is a lower alkoxy group, a compound of the general formula (Id), wherein $R^1$ and $Z^1$ are as defined above, is reacted with a $C_{1-4}$ diazoalkane or is treated with an alkanol in the presence of a catalytic amount of an acid.

The compounds of the general formula (III) wherein $R^1$ and $Z^1$ form together a double bond are known and commercially available substances. These compounds can be converted by known reductive hydrogenation into the respective derivatives wherein $R^1$ is hydrogen or lower alkoxy and $Z^1$ stands for hydrogen. The 3-oxo-esters of the general formula (II) as well as 2-acetyl-butyrolactone are commercially available substances. These compounds are converted into the respective dianions by reacting them with a base. The reaction proceeds through the formation of the respective monoanions. It is preferred to apply an alkali metal salt of a $C_{1-5}$ aliphatic alcohol, a $C_{1-4}$ alkyl lithium or a lithium compound of a $C_{2-8}$ dialkylamine as base to form the monoanion. The monoanions can be converted into dianions by treating them preferably with a $C_{1-4}$ alkyl lithium, phenyl lithium or a lithium compound of a $C_{2-8}$ dialkylamine. According to a preferred method the monoanions are formed with sodium hydride in an ether-type solvent (such as diethyl ether, dioxane, tetrahydrofuran) at low temperatures, such as at $-30°$ to $+20°$ C. The dianions are formed preferably with butyl lithium base in tetrahydrofuran solvent at a temperature of $-40°$ to $+20°$ C.

It is not necessary to separate the monoanions and dianions from the reaction mixture, since they can be reacted with the citronellal derivatives of the general formula (III) directly in the medium where they were formed. This reaction can also be performed preferably in an ether-type solvent at a temperature of $-40°$ to $+30°$ C. The resulting compounds of the general formula (Ia) or (Ib) can be separated from the reaction mixture by column chromatography.

According to methods (c) and (d) of the invention the compounds of the general formulae (Ia) and (Ib) are subjected to elimination reaction to form the respective products of the general formulae (Ic) and (Id). The reaction can be performed preferably with alcoholic hydrochloric acid at room temperature, or with a a p-toluenesulfonic acid derivative, particularly p-toluenesulfonyl chloride, in the presence of a base. The resulting product can be separated from the reaction mixture and purified by column chromatography or vacuum distillation.

According to methods (e) and (f) of the invention the compounds of the general formulae (Ia) and (Ib) are reacted with a lower diazoalkane to form the respective products of the general formulae (Ie) and (If). It is preferred to apply ether as reaction medium in this step.

According to methods (g) and (h) of the invention the compounds of the general formulae (Ic) and (Id) are reacted with a lower diazoalkane or are treated with a lower alkanol in the presence of a catalytic amount of an acid to form the respective compounds of the general formulae (Ig) and (Ih). The reaction is performed preferably by applying a strong mineral acid, such as hydrochloric acid, and a lower aliphatic alkanol, such as methanol or ethanol.

The compositions according to the invention possess valuable and specific juvenilhormone effects. The specific effects, i.e. somewhat higher activities observed on certain insect types, can be attributed to the presence of certain specific functional groups. According to our experiences the ethyl ester derivatives are the most active against butterflies, whereas the highest activity against flies can be observed with the isopropyl ester compounds. The tert.-butyl esters proved to be particularly effective against housefly (*Musca domestica*), the lactone and cyclopentane derivatives can be applied, however, with good results for the same purpose, too.

The insecticidal activities of the compositions according to the invention are demonstrated by the results of the following tests.

Test 1

Test insect: *Pieris brassicae*

24 hours' old cabbage butterfly (*Pieris brassicae*) caterpillars in the last development stage ($L_5$), bred on pot-grown savoy under laboratory conditions, were applied as test animals. The compounds to be tested were applied in doses of 100 μg/caterpillar, by dropping a solution of the active agent in 2 μl of acetone onto the dorsal surface of the larvae (topical treatment). The caterpillars treated with the active agents were placed into glasses covered with linen, fed with savoy leaves and, as before, were kept at 25° C. with a daily illumination period of 18 hours. The results were evaluated after deplumation or pupation, by counting the specifically malformed entities which converted into transition forms between larva and pupa and calculating their ratio, furthermore by calculating the average degree of malformation of these intermediates. This latter value was calculated by using an intermediate score ranging from 0 to 5, with 0 corresponding to the normal pupa and 5 to the so-called "superlarva" stage. The results are listed in Table 1.

TABLE 1

| Compound (No. of Example) | Number of larvae treated | Larva-pupa transition form, % | Average degree of malformation |
|---|---|---|---|
| 11 | 10 | 100 | 1.70 |
| 6 | 12 | 100 | 2.33 |
| 7 | 12 | 100 | 1.67 |

Test 2

Test insect: *Sarcophaga bullata*

The tests were performed on fleshfly (*Sarcophaga bullata*) larvae in the last development stage ($L_3$), bred on beef liver at 26° to 28° C. Prior to the treatment the larvae, which had finished their food intake and emptied their intestinal canal, were kept between wet tissue papers for 5 days at 5°-6° C., in order to synchronize the development of the larvae. The doses of the compounds to be tested, as given in Table 2, were dissolved in 2 μl of acetone, and the solution was dropped onto the body surface of the larvae (topical treatment). The larvae and the pupae formed therefrom were maintained in Petri dishes at 25° C.

The results were evaluated after the emergence of the flies by calculating the ratio of the pupae perished owing to specific disturbances in development. The degree of activity was calculated according to the Schneider-Orelli formula, in which the actual mortality is corrected with the mortality observed for the control insects treated with acetone only. The results are listed in Table 2.

TABLE 2

| Compound (No. of Example) | Dose (μg/insect) | Number of larvae treated | Mortality of the pupae, % | Activity, % (Schneider-Orelli) |
|---|---|---|---|---|
| 11 | 100 | 15 | 93.3 | 92.9 |
|    | 10  | 20 | 40.0 | 36.8 |
| 6  | 100 | 14 | 35.7 | 32.3 |
|    | 10  | 20 | 25.0 | 21.1 |
| 7  | 100 | 17 | 70.6 | 69.1 |
|    | 10  | 17 | 41.2 | 38.1 |

Test 3

Test insect: *Musca domestica*

The tests were performed on white pupae of housefly (*Musca domestica*) not elder than 1 hour, bred on culture broth under laboratory conditions at 25° to 28° C. The doses of the compounds to be tested, as given in Table 3, were dissolved in 1 μl of 96% ethanol, and the solution was dropped onto the body surface of the white pupae (topical treatment). The treated pupae were maintained in Petri dishes at 25° C.

The results were evaluated by calculating the ratio of the pupae perished as a consequence of a specific development disturbance (nipping in the pupa). The degree of activity was calculated according to the Schneider-Orelli formula, in which the actual mortality is corrected with the mortality observed for the control insects treated with acetone only. The results are listed in Table 3.

TABLE 3

| Compound (No. of Example) | Dose (μg/insect) | Number of larvae treated | Mortality of the pupae, % | Activity, % (Schneider-Orelli) |
|---|---|---|---|---|
| 8  | 10  | 20 | 85 | 84.21 |
|    | 3   | 20 | 65 | 63.16 |
|    | 1   | 20 | 60 | 52.63 |
|    | 0.3 | 20 | 10 | 5.26  |
| 23 | 10  | 10 | 60 | 60.00 |
|    | 3   | 10 | 40 | 40.00 |
|    | 1   | 10 | 20 | 20.00 |
|    | 0.3 | 10 | 20 | 20.00 |
| 7  | 10  | 20 | 65 | 63.16 |
|    | 3   | 20 | 20 | 15.78 |
|    | 1   | 20 | 15 | 10.53 |
| 20 | 10  | 20 | 65 | 63.16 |
|    | 3   | 20 | 45 | 42.11 |
|    | 1   | 20 | 35 | 31.58 |
|    | 0.3 | 20 | 25 | 21.05 |
|    | 0.1 | 20 | 20 | 15.79 |
| 8  | 10  | 20 | 50 | 44.44 |
|    | 3   | 10 | 30 | 22.22 |
|    | 1   | 10 | 30 | 22.22 |
|    | 0.3 | 10 | 20 | 11.11 |
| 18 | 10  | 20 | 20 | 15.79 |
| 12 | 10  | 20 | 50 | 47.37 |
|    | 3   | 20 | 40 | 36.84 |
|    | 1   | 20 | 35 | 31.58 |
|    | 0.3 | 20 | 35 | 31.58 |
|    | 0.1 | 20 | 10 | 5.26  |

The invention is elucidated in detail by the aid of the following non-limiting Examples.

EXAMPLE 1

Preparation of an emulsifiable concentrate 10 parts by weight of ethyl-(5-hydroxy-7,11-dimethyl-11-methoxy-3-oxo-dodecanoate) are dissolved in 9 parts by weight of xylene, and 1 part by weight of a mixture of an anionic and a non-ionic surfactant (i.e. a 2:3 mixture of Atlox 3386 and Atlox 4851) is added to the solution. The mixture is homogenized. An emulsifiable concentrate containing 50% by weight of active agent (50 EC) is obtained, which can be diluted with water to form a spray liquid.

EXAMPLE 2

Preparation of microgranulates 26 parts by weight of powdered kaoline, 15 parts by weight of potato starch and/or corn starch and 1 part by weight of talc are homogenized with 5 parts by weight of ethyl-[11-methoxy-3-oxo-7,11-dimethyl-4(E)-dodecenoate], and 0.5 parts by weight of Tween 80 (polyoxyethylene-sorbitane monooleate) are added to the mixture. 2.5 parts by weight of gelatine are swollen in 10 parts by weight of water, then additional 15 parts by weight of water are added, and the gelatine is dissolved under heating. The resulting solution is admixed with the above powder mixture. The wet mass is homogenized, granulated on a sieve (14 to 16 mesh), the granulates are dried and then sieved again. A microgranular composition containing 10% by weight of active agent is obtained.

EXAMPLE 3

One proceeds as described in Example 1 or 2, with the difference that another compound of the general formula (I) is applied as active agent.

EXAMPLE 4

Preparation of isopropyl (5-hydroxy-3-oxo-7,11-dimethyl-dodecanoate) (Ia, $R^1=Z^1=Z^3=Z^4=Z^5=H$, $R^3=iC_3H_7$)

3.0 g of sodium hydride (0.1 mole, 80% oily suspension) are added to a solution of 6.45 g (6.5 ml, 0.045 moles) of isopropyl acetoacetate in 25 ml of dry tetrahydrofuran at 0° C., and the mixture is stirred at 0° C. for 0.5 hours. A solution of 3.2 g (0.05 moles) of butyl lithium in 31 ml of hexane (i.e. a 1.63 molar butyl lithium solution in hexane) is added dropwise to the reaction mixture under cooling, and the resulting solution is stirred at 0° C. for 0.5 hours. Thereafter a solution of 7.8 g (0.05 moles) of 6,7-dihydrocitronellal in 10 ml of dry tetrahydrofuran is added dropwise to the mixture, and the resulting mixture is stirred at room temperature for 15 hours.

The reaction mixture is acidified to pH 4 with 10% hydrochloric acid, the upper organic phase is separated, and the aqueous phase is extracted in two portions with a total amount of 50 ml of ether. The organic solutions are combined, washed with 15 ml of saturated aqueous sodium chloride solution, dried over magnesium sulfate, and ether is evaporated under vacuo. The residue is purified by column chromatography (adsorbent: Kieselgel 60, solvent: a 10:0.5 mixture of benzene and acetone) to obtain 9 g (66%) of the aimed compound; $R_f=0.34$.

Analsysis: Calculated for $C_{17}H_{32}O_4$ (m.wt.: 300.42): C: 67.96%, H: 10.74%; Found: C: 67.56%, H: 10.53%.

IR (NaCl): 3300, 1740, 1705, 1380, 1360, 1250, 1100 cm$^{-1}$.

NMR (CCl$_4$): 0.85 (9H, m), 1–1.8 (10H, m), 2.65 (2H, d, J=6 Hz), 2.95 (1H, m), 3.45 (1H, m), 5 (1H, h, J=6 Hz) ppm.

EXAMPLE 5

Preparation of ethyl (3-oxo-5-hydroxy-7,11-dimethyldodecanoate (Ia, $R^1=Z^1=Z^3=Z^4=Z^5=H$, $R^3=C_2H_5$)

A suspension of 1.65 g of sodium hydride (0.055 moles, 80% oily dispersion) in 20 ml of dry tetrahydrofuran is cooled to $-30°$ C., and 6.5 g (0.05 moles) of ethyl acetoacetate (II, R=C$_2$H$_5$) are added dropwise under vigorous stirring. 31.5 ml of a 1.75 molar solution of butyl lithium in hexane (=0.055 moles of butyl lithium) are added to the mixture at $-20°$ C. under argon atmosphere, and the resulting mixture is stirred for 15 minutes. Thereafter 7.8 g (0.05 moles) of dihydrocitronellal are added dropwise to the mixture at $-20°$ C. within 0.5 hours, and the resulting mixture is stirred at $-20°$ C. for further 0.5 hours. The mixture is allowed to warm to room temperature, stirred for one hour, and then admixed with a mixture of 120 ml of 1 n hydrochloric acid and 40 ml of saturated aqueous sodium chloride solution. The resulting mixture is extracted with ether, the ethereal solution is washed with water, 1 n hydrochloric acid, water, 5% aqueous sodium hydrocarbonate solution and then with water again, dried over magnesium sulfate, the solvent is evaporated in vacuo, and the residue is purified by column chromatography (adsorbent: Kieselgel 40, solvent: a 10:1 mixture of benzene and acetone). 9.5 g (66.4%) of the aimed compound are obtained.

Analysis: Calculated for C$_{16}$H$_{30}$O$_4$ (m.wt.: 286.42): C: 67.09%, H: 10.56%; Found: C: 66.92%, H: 10.72%.

IR (NaCl): 3450, 1740, 1650 cm$^{-1}$.

NMR (CDCl$_3$): 0.7–2 (22H, m), 2.55 (1H, m), 2.6 (1H, m), 3.5 (1H, m), 4.15 (2H, q, J=6 Hz) ppm.

EXAMPLE 6

Preparation of ethyl (5-hydroxy-7,11-dimethyl-11-methoxy-3-oxo-dodecanoate) (Ia, $R^1=CH_3O$, $Z^1=Z^3=Z^4=Z^5=H$, $R^3=C_2H_5$)

1.23 g (1.2 ml, 0.0095 moles) of ethyl acetoacetate are added dropwise, under stirring to a 0° C. suspension of 0.54 g of sodium hydride (0.011 moles, a 50% oily dispersion) in 25 ml of dry tetrahydrofuran, maintained under argon atmosphere. 6 ml of a 5% etheral methyl lithium solution (=0.011 moles of methyl lithium) are added to the resulting pale yellow solution at 0° C., and the mixture is stirred for 30 minutes. Thereafter 1.77 g (0.0095 moles) of 7-methoxy-6,7-dihydrocitronellal are added dropwise to the mixture, and the reaction mixture is stirred at room temperature for 2 hours.

The mixture is poured onto ice water, the mixture is acidified with some drops of hydrochloric acid, and then extracted with a total amount of 100 ml of methylene chloride in three portions. The extracts are combined, washed with water, dried, the solvent is evaporated, and the residue is purified by column chromatography (adsorbent: Kieselgel 60, solvent: a 10:0.5 mixture of benzene and ethanol). 2.25 g (75%) of the aimed compound are obtained as a pale yellow oil, $R_f=0.37$ (developed with a 10:0.7 mixture of benzene and ethanol).

Analysis: Calculated for C$_{17}$H$_{32}$O$_5$ (m.wt: 316.43): C: 64.52%, H: 10.19%; Found: C: 64.78%, H: 10.02%.

IR (NaCl): 3350, 1730, 1705, 1630, 1380, 1360, 1300, 1250, 1220, 1140, 1080, 1020 cm$^{-1}$.

NMR (CDCl$_3$): 0.9 (3H, d, J=6 Hz), 1.1–1.8 (18H, m), 2.65 (2H, d, J=6 Hz), 3.15 (3H, s), 3.45 (1H, s), 4.2 (2H, q, J=6 Hz) ppm.

Mass spectrum: M+ 316 (1%), 287 (10), 172 (12), 228 (30), 225 (10), 200 (16), 180 (22), 115 (8), 87 (100), 73 (100).

EXAMPLE 7

Preparation of isopropyl (5-hydroxy-7,11-dimethyl-11-methoxy-3-oxo-dodecanoate) (Ia, $R^1=CH_3O$, $Z^1=Z^3=Z^4=Z^5=H$, $R^3=iC_3H_7$)

Method (a)

6.63 g (0.046 moles) of isopropyl acetoacetate are added dropwise to a suspension of 2 g of sodium hydride (0.066 moles, a 80% oily dispersion) in 50 ml of dry tetrahydrofuran at 0° C., and the resulting mixture is stirred at 0° C. for 20 minutes, whereupon a pale yellow solution of the respective sodium salt is formed. A 15–20% hexane solution of butyl lithium, containing 3.2 g (0.05 moles) of butyl lithium, is added to the mixture at 0° C., and the resulting solution is stirred for 30 minutes. Thereafter 9.5 g (0.051 moles) of 7-methoxy-6,7-dihydrocitronellal are added dropwise to the pale yellow solution of the salt at 0° C., and the resulting mixture is stirred at room temperature for 3 hours.

The reaction mixture is poured into 100 ml of ice water, and extracted in three portions with a total amount of 150 ml of methylene chloride. The extract is washed with water, 3 n aqueous hydrochloric acid and then with water again, dried over magnesium sulfate, the solvent is evaporated, and the residue is purified by column chromatography (adsorbent: Kieselgel 60, solvent: a 10:0.5 mixture of benzene and isopropanol). 12.65 g (83.2%) of the aimed compound are obtained; $R_f=0.35$ (developed with a 10:0.5 mixture of benzene and methanol).

Analysis: Calculated for C$_{18}$H$_{34}$O$_5$ (m.wt.: 330.45): C: 65.42%, H: 10.37%; Found: C: 65.65%, H: 10.52%.

IR (NaCl): 3400, 1725, 1710, 1640, 1260, 1230, 1140, 1100, 1080 cm$^{-1}$.

NMR (CDCl$_3$): 0.95 (3H, d, J=6 Hz), 1.1–1.8 (21H, m), 2.65 (2H, d, J=6 Hz), 3.2 (3H, s), 3.4 (1H, s), 4.15 (1H, m), 5.1 (1H, m) ppm.

Mass spectrum: M+ 330 (1%), 299 (15), 284 (12), 257 (11), 258 (10), 240 (17), 221 (40), 144 (100).

Method (b)

1.27 g (1.3 ml, 0.0089 moles) of isopropyl acetoacetate are added dropwise to a suspension of 0.6 g of sodium hydride (0.0125 moles, a 50% oily dispersion) in 25 ml of dry tetrahydrofuran at 0° C., and the resulting mixture is stirred for 20 minutes at 0° C. under argon atmosphere. 6 ml of a 5% etheral methyl lithium solution (=0.011 moles of methyl lithium) are added to the pale yellow solution, and the resulting mixture is stirred for 30 minutes. Thereafter 1.7 g (0.009 moles) of 7-methoxy-6,7-dihydrocitronellal are added to the pale yellow solution of the sodium lithium di-salt at 0° C., and the mixture is stirred at room temperature for 2 hours.

The reaction mixture is poured onto about 50 g of crushed ice, extracted with methylene chloride, the extract is washed with water, dried over magnesium sulfate, and the solvent is distilled off. The residue is purified by column chromatography to obtain 2.10 g (71.7%) of the aimed compound, which is identical with the product prepared according to Method (a).

Method (c)

2.6 ml (2.56 g, 0.018 moles) of isopropyl acetoacetate are dissolved in 10 ml of dry tetrahydrofuran, the solution is cooled to 0° C., and 1.02 g of a 80% oily sodium hydride dispersion (=0.0428 moles of sodium hydride) are added. The reaction mixture is stirred at 0° C. for 0.5 hours under argon atmosphere.

An etheral methyl lithium solution, prepared from 1.25 ml (2.84 g, 0.02 moles) of methyl iodide and 0.28 g (0.04 moles) of lithium in 15 ml of dry ether, is added to the reaction mixture at such a rate that the temperature of the mixture does not raise above 0° C. The mixture is stirred at 0° C. for additional 0.5 hours, and then a solution of 4.0 ml (0.0215 moles) of 7-methoxy-6,7-dihydrocitronellal in 2 ml of dry tetrahydrofuran is added. The mixture is stirred at room temperature under argon atmosphere for 15 hours.

The reaction mixture is cooled to 0° C., acidified to about pH 5 with 10% hydrochloric acid, the upper organic phase is separated, and the aqueous phase is extracted in two portions with a total amount of 20 ml of ether. The organic phases are combined, washed with 10 ml of a saturated aqueous sodium chloride solution, dried over magnesium sulfate, and the solvent is evaporated in vacuo. The oily residue is purified by column chromatography to obtain 2.50 g (75%) of the product, which is identical with the compound obtained according to Method (a).

EXAMPLE 8

Preparation of tert.-butyl
(5-hydroxy-7,11-dimethyl-11-methoxy-3-oxo-dodecanoate) (Ia, $R^1$=CH$_3$O, $Z^1$=$Z^3$=$Z^4$=$Z^5$=H, $R^3$=tert.C$_4$H$_9$).

1.45 g (0.009 moles) of tert.-butyl acetoacetate are added dropwise to a suspension of 0.6 g of sodium hydride (0.0125 moles, a 50% oily dispersion) in 20 ml of dry tetrahydrofuran t 0° C., and the resulting suspension is stirred at 0° C. for 30 minutes under argon atmosphere. 6 ml of a 5% etheral methyl lithium solution (=0.011 moles of methyl lithium) are added to the resulting pale yellow solution, and the mixture is stirred for 30 minutes. 1.7 g (0.009 moles) of 7-methoxy-6,7-dihydrocitronellal are added dropwise to the resulting pale yellow solution of the dianion at 0° C., and the resulting mixture is stirred at room temperature for two hours.

The reaction mixture is poured onto ice water, acidified with a small amount of hydrochloric acid, and extracted with methylene chloride. The extract is washed with water, dried, the solvent is distilled off, and the residue is purified by column chromatography. 2.23 g (72%) of the aimed compound are obtained; $R_f$=0.38 (developed with a 10:0.5 mixture of benzene and methanol).

Analysis: Calculated for $C_{19}H_{36}O_5$ (m.wt.: 344.48): C: 66.24%, H: 10.53%; Found: C: 66.43%, H: 10.26%.

IR (NaCl): 3400, 1700, 1380, 1360, 1240, 1140, 1070 cm$^{-1}$.

NMR (CDCl$_3$): 0.9 (3H, d, J=6 Hz), 1.1–1.8 (15H, m), 1.5 (9H, s), 2.65 (2H, d, J=6 Hz), 3.15 (3H, s), 3.4 (1H, m) ppm.

EXAMPLE 9

Preparation of
ethyl[3-oxo-7,11-dimethyl-4(E)-dodecenoate](Ic, $R^1$=$Z^1$=$Z^3$=$Z^4$=$Z^5$=H, $R^3$=C$_2$H$_5$)

A mixture of 2.86 g (0.01 moles) of ethyl (3-oxo-5-hydroxy-7,11-dimethyl-dodecanoate) and 10 ml of a 1 n ethanolic hydrochloric acid solution is stirred at room temperature for 12 hours. The solvent is distilled off in vacuo, and the residue is purified by column chromatography (adsorbent: Kieselgel 40, solvent: a 10:0.5 mixture of benzene and acetone). 1.7 g (63.0%) of the aimed compound are obtained.

Analysis: Calculated for $C_{16}H_{28}O_3$ (m.wt.: 268.38): C: 71.60%, H: 10.51%; Found: C: 71.32%, H: 10.42%.

IR (NaCl): 1740, 1680, 1650, 1620 cm$^{-1}$.

NMR (CDCl$_3$): 0.7–2.3 (22H), 3.6 (1H, d, J=4 Hz), 4.2 (2H, q, J=6 Hz) ppm.

EXAMPLE 10

Preparation of
isopropyl[3-oxo-7,11-dimethyl-4-(E)-dodecenoate](Ic, $R^1$=$Z^1$=$Z^3$=$Z^4$=$Z^5$=H, $R^3$=iC$_3$H$_7$)

2.9 g (0.0096 moles) of isopropyl (5-hydroxy-3-oxo-7,11-dimethyl-dodecanoate) are dissolved in 15 ml of isopropanol containing 6% of hydrochloric acid, and the mixture is allowed to stand at room temperature for 4 days. The solvent is distilled off in vacuo, and the residue is purified by column chromatography (adsorbent: Kieselgel 60, solvent: a 7:3 mixture of hexane and acetone). 1.8 g (67%) of the aimed compound are obtained.

IR (NaCl): 1730, 1650, 1620, 1600, 1360, 1250, 1230, 1100 cm$^{-1}$.

NMR (CCl$_4$): 0.9 (9H, m), 1.1–1.8 (14H, m), 2–2.2 (2H, m), 3.5 (1H, m), 4.8 (1H, m), 5 (1H, q), 5.2–6.8 (2H, m) ppm.

EXAMPLE 11

Preparation of
ethyl[11-methoxy-3-oxo-7,11-dimethyl-4(E)-dodecenoate](Ic, $R^1$=CH$_3$O, $Z^1$=$Z^3$=$Z^4$=$Z^5$=H, $R^3$=C$_2$H$_5$)

1 ml of ethanol saturated with hydrochloric acid is added to a solution of 1.56 g (0.005 moles) of ethyl (5-hydroxy-11-methoxy-3-oxo-7,11-dimethyl-dodecanoate) in 10 ml of dry ethanol, and the mixture is allowed to stand overnight. The solvent is evaporated in vacuo, and the residue is purified by chromatography (adsorbent: Kieselgel 60, solvent: a 10:0.5 mixture of benzene and ethanol). 0.94 g (63.1%) of the compound are obtained; $R_f$=0.52 (developed with a 10:0.5 mixture of benzene and ethanol).

Analysis: Calculated for $C_{17}H_{30}O_4$ (m.wt. 298.41): C: 68.42%, H: 10.13%; Found: C: 68.81%, H: 10.40%.

IR (NaCl): 1725, 1700, 1660, 1610, 1380, 1360, 1240, 1140, 1070 cm$^{-1}$.

NMR (CDCl$_3$): 0.9 (3H, d, J=6 Hz), 1.1–1.8 (16H, m), 2.2 (2H, m), 3.2 (3H, s), 3.6 (1H, m), 4.2 (2H, q, J=6 Hz), 5–7 (3H, m) ppm.

EXAMPLE 12

Preparation of
isopropyl[11-methoxy-3-oxo-7,11-dimethyl-4(E)-dodecenoate](Ic, $R^1$=CH$_3$O, $Z^1$=$Z^3$=$Z^4$=$Z^5$=H, $R^3$=iC$_3$H$_7$)

3.6 g (0.01 moles) of isopropyl (5-hydroxy-7,11-dimethyl-11-methoxy-3-oxo-dodecanoate) are dissolved in 20 ml of dry isopropanol, 2 ml of isopropanol saturated with hydrochloric acid are added, and the mixture is allowed to stand at room temperature overnight. The solvent is distilled off in vacuo, the residue is dissolved in 20 ml of ether, the etheral solution is washed with distilled water, dried, and the solvent is evaporated. The residue is purified by chromatography (adsorbent: Kieselgel 60, solvent: a 10:0.5 mixture of benzene and isopropanol). 1.9 g (61%) of the aimed compound are obtained; $R_f$=0.7 (developed with a 10:1 mixture of benzene and isopropanol).

Analysis: Calculated for C$_{18}$H$_{32}$O$_4$ (m.wt. 312.44): C: 69.19%, H: 10.33%; Found: C: 68.90%, H: 10.12%.

IR (NaCl): 1720, 1650, 1620, 1590, 1380, 1360, 1230, 1160, 1140, 1090, 960 cm$^{-1}$.

NMR (CDCl$_3$): 0.95 (3H, d, J=6 Hz), 1.1–1.8 (19H, m), 2.1 (2H, m), 3.32 (3H, s), 3.6 (1H, m), 5 (1H, m), 5.2–7 (3H, m) ppm.

Mass spectrum: M+ 312 (8), 297 (5), 280 (40), 266 (35), 253 (20), 238 (20), 221 (40), 198 (8), 179 (25), 161 (45), 73 (100), 43 (80).

EXAMPLE 13

Preparation of
tert.-butyl[11-methoxy-3-oxo-7,11-dimethyl-4(E)-dodecenoate](Ic, $R^1$=CH$_3$O, $Z^1$=$Z^3$=$Z^4$=H, $R^3$=tert.—C$_4$H$_9$)

0.75 g (0.0039 moles) of p-toluenesulfonyl chloride are added to a solution of 1.0 g (0.0029 moles) of tert.-butyl (5-hydroxy-11-methoxy-3-oxo-7,11-dimethyl-dodecanoate) in 2 ml of dry pyridine, and the mixture is allowed to stand at room temperature for 48 hours. The reaction mixture is poured onto ice, extracted with methylene chloride, the extract is washed with cold water, 3 n aqueous hydrochloric acid and then with water again, dried over magnesium sulfate, and the solvent is distilled off in vacuo. The residue is purified by chromatography (adsorbent: Kieselgel 60, solvent: a 10:0.5 mixture of benzene and tert.-butanol). 0.52 g (55%) of the aimed compound are obtained; $R_f$=0.6 (developed with a 10:0.5 mixture of benzene and tert.-butanol).

Analysis: Calculated for C$_{19}$H$_{34}$O$_4$ (m.wt. 326.46): C: 69.90%, H: 10.50%; Found: C: 69.52%, H: 10.41%.

NMR (CDCl$_3$): 0.9 (3H, d, J=6 Hz), 1.1–1.8 (22H, m), 2.2 (2H, m), 3.1 (3H, s), 3.5 (1H, m), 5.4–7 (3H, m) ppm.

EXAMPLE 14

Preparation of
isopropyl[3,11-dimethoxy-7,11-dimethyl-2(Z),4(E)-dodecadienoate](Ig, $R^1$=CH$_3$O, $Z^1$=$Z^3$=H, $Z^4$+D=double bond, C=CH$_3$O, $R^3$=iC$_3$H$_7$)

An etheral diazomethane solution containing 0.01 moles of diazomethane is added to a solution of 0.7 g (0.0022 moles) of isopropyl[11-methoxy-3-oxo-7,11-dimethyl-4(E)-dodecenoate] in 5 ml of dry ether, and the mixture is allowed to stand at room temperature for 5 hours. The solvent is evaporated in vacuo, the residue is taken up with ether, and the solution is filtered through a short column filled with Kieselgel 60 adsorbent. Ether is evaporated from the effluent to obtain 0.65 g (90.5%) of the aimed compound as a pale yellow oil; $R_f$=0.45 (developed with a 10:0.7 mixture of benzene and methanol).

Analysis: Calculated for C$_{19}$H$_{34}$O$_4$ (m.wt. 326.46): C: 69.90%, H: 10.50%, Found: C: 68.98%, H: 10.07%.

NMR (CCl$_4$): 0.95 (3H, d, J=6 Hz), 1.1–1.8 (19H, m), 2.2 (2H, m), 3.2 (3H, s), 3.75 (3H, s), 5.1 (1H, m), 5.2–7.3 (3H, m) ppm.

EXAMPLE 15

Preparation of isopropyl (5-hydroxy-3-oxo-7,11-dimethyl-10-dodecenoate) (Ia, $R^1$+$Z^1$=double bond, $Z^3$=$Z^4$=$Z^5$=H, $R^3$=iC$_3$H$_7$.

6.3 g of sodium hydride (0.196 moles, a 75% oily dispersion) are added within 15 minutes to a cooled (−10° to 0° C.) solution of 12.8 g (13.0 ml, 0.089 moles) of isopropyl acetoacetate in 50 ml of dry tetrahydrofuran under argon atmosphere. The mixture is stirred at −10° C. for 0.5 hours, thereafter 62 ml of a 1.63 molar butyl lithium solution in hexane are added at such a rate that the temperature of the mixture does not raise above 0° C. The reaction mixture is stirred at 0° C. for 0.5 hours, then a solution of 16.53 g (0.108 moles) of citronellal in 15 ml of dry tetrahydrofuran is added. The mixture is stirred at room temperature for 14 hours, and then acidified to pH 4 with 10% aqueous hydrochloric acid under cooling. The upper organic phase is separated, and the aqueous phase is extracted in two portions with a total amount of 100 ml of ether. The organic solutions are combined, washed with saturated aqueous sodium chloride solution, dried over magnesium sulfate, and the solvent is distilled off under vacuo. The residue is purified by column chromatography (adsorbent: Kieselgel 60, solvent: a 10:1 mixture of benzene and ethyl acetate, $R_f$=0.55), 20.5 g (77.0%) of the aimed compound are obtained.

Analysis: Calculated for C$_{17}$H$_{30}$O$_4$ (m.wt. 298.41): C: 68.42%, H: 10.13%; Found: C: 68.19%, H: 10.44%.

IR (NaCl): 3350, 1730, 1705, 1630, 1370, 1360, 1250, 1100, 960 cm$^{-1}$.

NMR (CCl$_4$): 0.85 (3H, d, J=7 Hz), 1–2.2 (7H, m, CH, CH$_2$), 1.2 (6H, D, J=7 Hz), 1.5 (6H, m), 2.45 (2H, d, J=6 Hz), 3.2 (1H, m), 5 (2H, m) ppm.

EXAMPLE 16

Preparation of
isopropyl[3-oxo-7,11-dimethyl-5(E),10-dodecadienoate](Ic, $R^1$+$Z^1$=double bond, $Z^3$=$Z^4$=H, $R^3$=iC$_3$H$_7$)

1.5 g (0.0079 moles) of p-toluenesulfonyl chloride are added to a solution of 1 g (0.0033 moles) of isopropyl (5-hydroxy-3-oxo-7,11-dimethyl-10-dodecenoate) in 4.5 ml of dry pyridine, and the solution is allowed to stand at room temperature for 48 hours. The reaction mixture is poured onto 15 g of ice and extracted in three portions with a total amount of 45 ml of methylene chloride. The extracts are combined, washed with 3 n aqueous hydrochloric acid and water, dried over magnesium sulfate, and the solvent is distilled off in vacuo. The red, oily residue, weighing 0.95 g, is purified by column chromatography (adsorbent: Kieselgel 60, solvent: a 4:1 mixture of benzene and ethyl acetate). 0.6 g (64%) of the aimed compound are obtained.

IR (NaCl): 1710, 1650, 1620, 1600, 1380, 1360, 1220, 1160, 1100 cm$^{-1}$.

EXAMPLE 17

Preparation of methyl [3-(1-hydroxy-7-methoxy-3,7-dimethyl-octyl)-2-oxo-cyclopentanecarboxylate] (Ig, $R^1$=CH$_3$O, $Z^1$=$Z^5$=H, $Z^3$+$Z^4$=—CH$_2$CH$_2$—, $R^3$=CH$_3$)

Method (a)

2.3 g of sodium hydride (0.07 moles, a 75% oily dispersion) are added to a solution of 9.8 g (0.069 moles) of methyl (2-oxo-cyclopentanecarboxylate) in 50 ml of dry tetrahydrofuran and 50 ml of hexamethylphosphoric triamide, and the mixture is stirred under argon atmosphere until the gas evolution ceases (about one hour). The reaction mixture is cooled to 0° C., and 6.4 g (0.069 moles) of butyl lithium are introduced dropwise as a 15-20% hexane solution within 15 minutes under cooling. The resulting dark red solution of the sodium-lithium di-salt is cooled, a solution of 15.6 g (0.084 moles) of 7-methoxy-6,7-dihydrocitronellal in 640 ml of dry tetrahydrofuran is added to it under cooling, and then the mixture is stirred at room temperature for 10 hours.

200 ml of ether are added to the mixture, and the resulting mixture is shaken with 200 ml of a 10% aqueous hydrochloric acid. The ethereal phase is separated, washed with saturated aqueous sodium chloride solution, dried over magnesium sulfate, the solvent is distilled off, and the residue is purified by column chromatography (adsorbent: Kieselgel 40, solvent: a 10:1 mixture of benzene and acetone, $R_f$=0.50). 7.75 g (34.4%) of the aimed compound are obtained.

Analysis: Calculated for C$_{18}$H$_{32}$O$_5$ (m.wt. 328.44): C: 65.82%, H: 9.83%; Found: C: 66.01%, H: 9.69%.

IR (NaCl): 3360, 1715, 1640, 1600 cm$^{-1}$.

NMR (CCl$_4$): 2.1 (4H, m), 3 (3H, s), 3.6 (3H, s), 4 (1H, m) ppm.

Mass spectrum: M$^+$ (m/e) 328 (1), 238 (1.3), 224 (1.8), 173 (4.4), 149 (13.4), 109 (3.1), 96 (7.6), 85 (8.1), 81 (16.1), 73 (100).

Method (b)

A solution of 5.87 g (8.13 ml, 0.058 moles) of diisopropyl amine in 10 ml of dry tetrahydrofuran is cooled to −10° C., and 3.75 g (0.058 moles) of butyl lithium are added to the stirred mixture as a 15-20% hexane solution. The resulting mixture is stirred at 0° C. for 0.5 hours, and then a solution of 4.15 g (0.029 moles) of methyl (2-oxo-cyclopentanecarboxylate) in 20 ml of dry hexamethylphosphoric triamide is introduced dropwise at the same temperature. The mixture is stirred for 0.5 hours, and then a solution of 5.4 g (0.029 moles) of 7-methoxy-6,7-dihydrocitronellal in 20 ml of dry hexamethylphosphoric triamide is added to the solution of the lithium disalt at 0° C. Thereafter the mixture is stirred at room temperature for 2 hours.

The reaction mixture is diluted with 50 ml of ether, shaken with 50 ml of 10% aqueous hydrochloric acid, the etheral phase is separated, washed with water and saturated aqueous sodium chloride solution, dried over magnesium sulfate, and the solvent is distilled off. The residue is purified by column chromatography (adsorbent: Kieselgel 40, solvent: a 10:1 mixture of benzene and acetone, $R_f$=0.50). 2.1 g (22%) of the aimed compound are obtained; the product is identical with the substance prepared according to Method (a).

EXAMPLE 18

Preparation of methyl [3-(7-methoxy-3,7-dimethyloctylidene)-2-oxo-cyclopentanecarboxylate] (Ic, $R^1$=CH$_3$O, $Z^1$=H, $Z^3$+$Z^4$=—CH$_2$CH$_2$—, $R^3$=CH$_3$)

(Method (a)

0.5 ml of methanol saturated with hydrochloric acid are added to a solution of 1.45 g (0.0045 moles) of methyl [3-(1-hydroxy-7-methoxy-3,7-dimethyl-octyl)-2-oxo-cyclopentanecarboxylate] in 15 ml of dry methanol, and the mixture is allowed to stand at room temperature for 3 days. Methanol is distilled off from a steam bath in vacuo, and the residue is purified by column chromatography (adsorbent: Kieselgel 60, solvent: a 6:4 mixture of benzene and ethyl acetate, $R_f$=0.9). 0.70 g (51.5%) of the aimed compound are obtained.

Analysis: Calculated for C$_{18}$H$_{30}$O$_4$ (m.wt. 310.42): C: 69.65%, H: 9.75%; Found: C: 69.85%, H: 9.92%.

IR (NaCl): 1710, 1640, 1600, 1240, 1070 cm$^{-1}$.

NMR (CCl$_4$): 2.35 (4H, m), 3 (3H, s), 3.55 (3H, s), 5.5-6 (1H, t J=8 Hz) ppm.

Mass spectrum (m/e): M$^+$ 310 (3), 295 (4), 279 (3), 277 (46), 262 (14), 245 (46), 237 (13), 235 (37), 220 (28), 204 (15), 166 (17), 154 (33), 134 (20), 110 (23), 87 (45), 73 (100), 42 (100).

Method (b)

0.32 g (0.0017 moles) of p-toluenesulfonyl chloride are added to a solution of 0.5 g (0.00154 moles) of methyl [3-(1-hydroxy-7-methoxy-3,7-dimethyl-octyl)-2-oxo-cyclopentanecarboxylate] in 2 ml of dry pyridine, and the solution is allowed to stand at room temperature for 2 days. The reaction mixture is poured onto 10 g of crushed ice, and the resulting aqueous suspension is extracted in four portions with a total amount of 40 ml of methylene chloride. The extract is washed with 15 ml of 3 n aqueous hydrochloric acid and water, dried over magnesium sulfate, the solvent is distilled off, and the residue is purified by column chromatography. 0.25 g (53%) of the aimed compound are obtained; the product is identical with the substance obtained according to Method (a).

EXAMPLE 19

Preparation of 3-(9-methoxy-3-hydroxy-5,9-dimethyldecanoyl)-4-butyrolactone (Ib, $R^1$=CH$_3$O, $Z^1$=H)

3.2 g (0.025 moles) of 2-acetyl-butyrolactone are added dropwise to a stirred suspension of 1.0 g (0.033 moles) of sodium hydride (a 80% oily dispersion) in 35 ml of dry tetrahydrofuran at 0° C. under argon atmosphere, and the resulting mixture is stirred at 0° C. for 30 minutes. A 15-20% solution of butyl lithium in hexane, corresponding to an amount of 1.7 g (0.05 moles) of butyl lithium, is added to the resulting pale yellow solution of the sodium salt, and the resulting mixture is stirred at 0° C. for 30 minutes. 4.65 g (0.025 moles) of 7-methoxy-6,7-dihydrocitronellal are added dropwise to the resulting solution of the sodiumlithium disalt, and the mixture is stirred at room temperature for 2 hours. The reaction mixture is poured onto 100 ml of ice water containing some ml of hydrochloric acid, and the mixture is extracted in three portions with a total amount of 150 ml of methylene chloride. The extract is washed with water, dried, the solvent is distilled off, and the residue is purified by column chromatography. 5.4 g (68.7%) of the aimed compound are obtained as a pale yellow oil.

Analysis: Calculated for $C_{17}H_{30}O_5$ (m.wt. 314.41): C: 64.93%, H: 9.62%; Found: C: 64.96%, H: 9.98%.

IR (NaCl): 3400, 1760, 1720, 1650, 1370, 1230, 1200, 1140, 1070, 1020 cm$^{-1}$.

NMR (CDCl$_3$): 0.95 (3H, d, J=6 Hz), 1.1–1.8 (15H, m), 3.2 (3H, s), 3.7 (0.2H, m), 4.3 (2H, m) ppm.

EXAMPLE 20

Preparation of 3-[1,9-dimethoxy-5,9-dimethyl-2(E)decenylidene]-4-butyrolactone (Ih, $R^1$=CH$_3$O, $Z^1$=H)

1 ml of methanol saturated with hydrochloric acid is added to a solution of 1.05 g (0.0033 moles) of 3-(9-methoxy-3-hydroxy-5,9-dimethyl-decanoyl)-4-butyrolactone in 10 ml of dry methanol, and the mixture is allowed to stand at room temperature overnight. The solvent is distilled off in vacuo, the residue is dissolved in ether, the ethereal solution is washed with distilled water, dried, the solvent is distilled off, and the residue is purified by column chromatography (adsorbent: Kieselgel 60, solvent: a 10:0.1 mixture of benzene and methanol). 0.54 g (52.1%) of the aimed compound are obtained; R$_f$=0.8 (developed with a 10:0.2 mixture of benzene and methanol).

Analysis: Calculated for $C_{18}H_{30}O_4$ (m.wt. 310.42): C: 69.64%, H: 9.74%; Found: C: 69.42%, H: 9.58%.

IR (NaCl): 1700, 1645, 1590, 1380, 1360, 1340, 1260, 1230, 1180, 1010, 1080, 1040, 1000 cm$^{-1}$.

NMR (CDCl$_3$): 0.95 (3H, d, J=6 Hz), 1.1–1.9 (13H, m), 2.2 (2H, m), 3.02 (2H, q, J=9 Hz), 3.2 (3H, s), 3.75 (3H, s), 4.45 (2H, t, J=9 Hz), 6–7.3 (2H, m) ppm.

EXAMPLE 21

Preparation of 3-[9-methoxy-5,9-dimethyl-2(E)decenoyl]-4-butyrolactone (Id, $R^1$=CH$_3$O, $Z^1$=H)

1 ml of methanol saturated with hydrochloric acid is added to a solution of 2.1 g (0.007 moles) of 3-(9-methoxy-3-hydroxy-5,9-dimethyl-decanoyl)-4-butyrolactone in 15 ml of dry methanol, and the mixture is allowed to stand at room temperature for 12 hours. 2 ml of water are added to the mixture, and the mixture is stirred at room temperature for 5 hours. The solvent is distilled off in vacuo, the residue is taken up in ether, the ethereal solution is washed with water, dried, and the solvent is distilled off. The residue is purified by chromatography (adsorbent: Kieselgel 60, solvent: a 10:0.1 mixture of benzene and methanol). 1.4 g (70%) of the aimed compound are obtained; R$_f$=0.75 (developed with a 10:0.1 mixture of benzene and methanol).

Analysis: Calculated for $C_{17}H_{28}O_4$ (m.wt. 296.39): C: 68,89%, H: 9.52%; Found: C: 68.57%, H: 9.44%.

IR (NaCl): 1705, 1695, 1645, 1620, 1380, 1335, 1260, 1230, 1180, 1015, 1000 cm$^{-1}$.

NMR (CDCl$_3$): 0.95 (3H, d, J=6 Hz), 1.1–1.9 (13H, m), 2.2 (2H, m), 3.02 (2H, q, J=9 Hz), 3.2 (3H, s), 3.25 (1H, m), 4.45 (2H, t, J=9 Hz), 5.5–6.7 (3H, m) ppm.

EXAMPLE 22

Preparation of 3-[3-hydroxy-1,9-dimethoxy-5,9-dimethyl-(E)-decenylidene]-4-butyrolactone (If, $R^1$=CH$_3$O, $Z^1$=H)

An etherealdiazomethane solution containing 0.04 moles of diazomethane is added to a solution of 2.0 g (0.006 moles) of 3-(9-methoxy-3-hydroxy-5,9-dimethyl-decanoyl)-4-butyrolactone in 5 ml of dry ether, and the reaction mixture is allowed to stand at room temperature for 4 hours. The solvent is distilled off in vacuo, the residue is taken up with ether, and the solution is filtered through a short column filled with Kieselgel 60 adsorbent. Ether is removed from the effluent to obtain 1.2 g (63.2%) of the aimed compound as a pale yellow oil; R$_f$=0.62 (developed with a 10:0.4 mixture of benzene and methanol).

Analysis: Calculated for $C_{18}H_{32}O_5$ (m.wt. 328.44): C: 65.82%, H: 9.82%; Found: C: 65.61%, H: 9.53%.

IR (NaCl): 3400, 1730, 1720, 1700, 1650, 1630, 1370, 1230, 1200, 1140, 1100, 1070, 1020 cm$^{-1}$.

NMR (CDCl$_3$): 0.95 (3H, d, J=6 Hz), 1.1–1.8 (13H, m), 3.1 (3H, s), 3.65 (3H, s), 4.3 (2H, m) ppm.

EXAMPLE 23

Preparation of ethyl [5-hydroxy-3-methoxy-7,11-dimethyl-2(E)-dodecanoate] (Ie, $R^1$=$Z^1$=$Z^3$=$Z^5$=H, C=CH$_3$O, $R^3$=C$_2$H$_5$, $Z^4$+D=double bond)

An ethereal diazomethane solution containing 0.03 moles of diazomethane is added to a solution of 2.0 g (0.007 moles) of ethyl (5-hydroxy-7,11-dimethyl-3-oxo-dodecanoate) in 10 ml of dry ether, and the reaction mixture is allowed to stand at room temperature for 5 hours. The solvent is distilled off in vacuo, the residue is taken up with ether, and the solution is filtered through a short (5 cm) column filled with Kieselgel 60 adsorbent. Ether is evaporated from the effluent to obtain 1.1 g (57.9%) of the aimed compound as a pale yellow oil; R$_f$=0.75 (developed with a 10:0.5 mixture of benzene and methanol).

Analysis: Calculated for $C_{17}H_{32}O_4$ (m.wt. 300.43): C: 67.96%, H: 10.74%; Found: C: 67.98%, H: 10.42%.

NMR (CDCl$_3$): 0.95 (3H, d, J=6 Hz), 1.1–1.8 (15H, m), 2.2 (3H, m), 3.7 (3H, s), 4.0 (1H, m), 4.2 (2H, q, J=7 Hz) ppm.

What we claim is:

1. A compound of the formula (I),

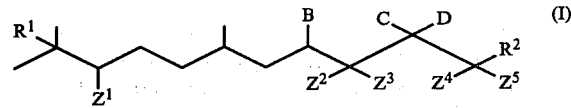

wherein
$R^1$ is hydrogen or a lower alkoxy group and
$Z^1$ is hydrogen, or
$R^1$ and $Z^1$ from together a double bond,
$Z^2$ is hydrogen and
B is hydroxy, or
$Z^2$ and B form together a double bond,
$Z^3$ and $Z^4$ each stand for hydrogen or they form together an ethylene group, or
$Z^4$ and D form together a double bond,
C is oxygen atom or a lower alkoxy group,
D is a valence bond if C stands for oxygen, or otherwise D forms a double bond together with $Z^4$ or $Z^5$,
$Z^5$ forms a double bond together with D or represents hydrogen, and
$R^2$ is a group of the formula —COOR$^3$, wherein R$^3$ is lower alkyl, or
$Z^5$ and $R^2$ form together a 1-oxo-2-oxa-tetramethylene group, with the proviso that if $Z^3$ and $Z^4$ form together an ethylene group, $R^2$ may stand only for a —$COOR^3$ group.

2. A compound of the formula (Ia),

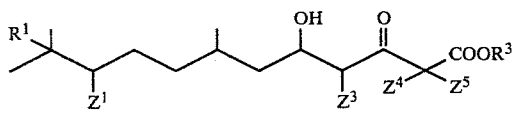
(Ia)

wherein $R^1$, $Z^1$, $Z^3$, $Z^4$, $Z^5$ and $R^3$ are as defined in claim 1.

3. Ethyl (5-hydroxy-7,11-dimethyl-11-methoxy-3-oxo-dodecanoate), isopropyl (5-hydroxy-7,11-dimethyl-11-methoxy-3-oxo-dodecanoate) and tert.-butyl (5-hydroxy-7,11-dimethyl-11-methoxy-3-oxo-dodecanoate).

4. A compound of the formula (Ic),

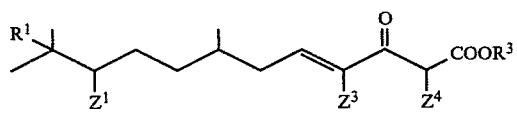
(Ic)

wherein $R^1$, $Z^1$, $Z^3$, $Z^4$ and $R^3$ are as defined in claim 1.

5. Ethyl [11-methoxy-3-oxo-7,11-dimethyl-4(E)-dodecenoate].

6. An insecticidal composition comprising as active agent a compound of the formula (I), wherein
$R^1$ is hydrogen or a lower alkoxy group and
$Z^1$ is hydrogen, or
$R^1$ and $Z^1$ form together a double bond,
$Z^2$ is hydrogen and
B is hydroxy, or
$Z^2$ and B form together a double bond,
$Z^3$ and $Z^4$ each stand for hydrogen or they form together an ethylene group, or
$Z^4$ and D form together a double bond,
C is oxygen atom or a lower alkoxy group,
D is a valence bond if C stands for oxygen, or otherwise D forms a double bond together with $Z^4$ or $Z^5$,
$Z^5$ forms a double bond together with D or represents hydrogen, and
$R^2$ is a group of the general formula —$COOR^3$, wherein $R^3$ is lower alkyl, or
$Z^5$ and $R^2$ form together a 1-oxo-2-oxa-tetramethylene group, with the proviso that if $Z^3$ and $Z^4$ form together an ethylene group, $R^2$ may stand only for a —$COOR^3$ group, in an amount of 0.01 to 96% by weight, together with an inert carrier or diluent conventionally utilized in such compositions.

7. An insecticidal composition as set forth in claim 6, wherein the active agent is a compound of the formula (Ia)

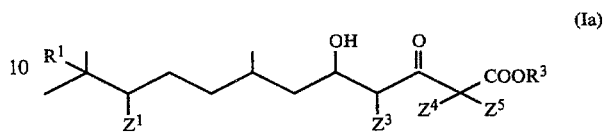
(Ia)

and wherein
$R^1$ is hydrogen or a lower alkoxy group and
$Z^1$ is hydrogen, or
$R^1$ and $Z^1$ form together a double bond,
$Z^3$ and $Z^4$ each stand for hydrogen or they form together an ethylene group,
$Z^5$ represents hydrogen, and
$R^3$ is lower alkyl.

8. An insecticidal composition as set forth in claim 6, wherein the active agent is selected from the group consisting of ethyl (5-hydroxy-7,11-dimethyl-11-methoxy-3-oxo-dodecanoate), isopropyl (5-hydroxy-7,11-dimethyl-11-methoxy-3-oxo-dodecanoate) and tert.-butyl (5-hydroxy-7,11-dimethyl-11-methoxy-3-oxo-dodecanoate).

9. An insecticidal composition as set forth in claim 6, wherein the active agent is a compound of the formula (Ic),

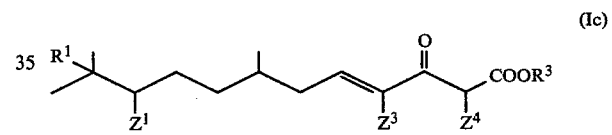
(Ic)

wherein
$R^1$ is hydrogen or a lower alkoxy group and
$Z^1$ is hydrogen, or
$R^1$ and $Z^1$ form together a double bond,
$Z^3$ and $Z^4$ each stand for hydrogen or they form together an ethylene group, and
$R^3$ is lower alkyl.

10. An insecticidal composition as set forth in claim 6, wherein the active agent is ethyl (11-methoxy-3-oxo-7,11-dimethyl-4(E)-dodecenoate).

11. An agricultural process for killing insects which comprises applying to plants or the soil surrounding the plants a composition as set forth in claims 6, 7, 8, 9 or 10.

* * * * *